(12) United States Patent
M'Kacher

(10) Patent No.: US 12,258,621 B2
(45) Date of Patent: Mar. 25, 2025

(54) HIGH-THROUGHPUT METHOD FOR DETECTING CHROMOSOMAL ABERRATIONS AND/OR TELOMERE ABERRATIONS

(71) Applicant: CELL ENVIRONMENT, Champigny-sur-Marne (FR)

(72) Inventor: Radhia M'Kacher, Champigny sur Marne (FR)

(73) Assignee: CELL ENVIRONMENT, Champigny-sur-Marne (FR)

( * ) Notice: Subject to any disclaimer, the term of this patent is extended or adjusted under 35 U.S.C. 154(b) by 989 days.

(21) Appl. No.: 17/277,507

(22) PCT Filed: Sep. 17, 2019

(86) PCT No.: PCT/EP2019/074870
§ 371 (c)(1),
(2) Date: Mar. 18, 2021

(87) PCT Pub. No.: WO2020/058268
PCT Pub. Date: Mar. 26, 2020

(65) Prior Publication Data
US 2022/0033887 A1  Feb. 3, 2022

(30) Foreign Application Priority Data
Sep. 18, 2018 (FR) .................................... 1858427

(51) Int. Cl.
*C12Q 1/6832* (2018.01)
*C12Q 1/6841* (2018.01)

(52) U.S. Cl.
CPC ......... *C12Q 1/6832* (2013.01); *C12Q 1/6841* (2013.01)

(58) Field of Classification Search
CPC .................................................. C12Q 1/6841
See application file for complete search history.

(56) References Cited

FOREIGN PATENT DOCUMENTS

| CN | 108004299 A | 5/2018 |
|---|---|---|
| JP | 2006-242618 A | 9/2006 |

(Continued)

OTHER PUBLICATIONS

De Jong, B., G. J. P. A. Anders, and Ingrid H. van der Meer. "Chromosome preparations from microplate cultures of man, dog, rat, and mouse." Human Genetics 33 (1976): 295-298. (Year: 1976).*

(Continued)

*Primary Examiner* — Aaron A Priest
*Assistant Examiner* — Tian Yu
(74) *Attorney, Agent, or Firm* — Maier & Maier, PLLC

(57) ABSTRACT

A high throughput method for detecting chromosomal aberrations and/or telomere aberrations using a biological sample of 150 μL to 200 μL including preparing a cytogenetic slide from the sample in a microplate, the mitotic index in the cytogenetic slide being 3 times higher on average than the conventional procedure of culturing cells in flasks with 10 to 20 mL of medium, simultaneously labeling the telomeres and centromeres with peptide nucleic acid probes with a hybridisation time from 30 minutes to 1.5 hours, flow image quantifying the fluorescence intensity of telomeres on interphase nuclei using a 10× magnification objective for overall telomere quantification, and automatically capturing the metaphase chromosomes to detect chromosomal aberrations and/or telomere aberrations in each chromosome. Also a high-throughput detection kit for quantifying telomeres and detecting chromosomal aberrations and/or telomere aberrations.

17 Claims, 14 Drawing Sheets

(56) References Cited

FOREIGN PATENT DOCUMENTS

| WO | 1997/14026 A2 | 4/1997 |
|---|---|---|
| WO | 1997/14026 A3 | 4/1997 |

OTHER PUBLICATIONS

M'kacher et al. New tool for biological dosimetry: reevaluation and automation of the gold standard method following telomere and centromere staining. Mutat Res. Dec. 2014; 770:45-53. doi: 10.1016/j.mrfmmm.2014.09.007. Epub Sep. 28, 2014. PMID: 25771869 (Year: 2014).*

Roukos V, Pegoraro G, Voss TC, Misteli T. Cell cycle staging of individual cells by fluorescence microscopy. Nat Protoc. Feb. 2015; 10(2):334-48. doi: 10.1038/nprot.2015.016. Epub Jan. 29, 2015. PMID: 25633629; PMCID: PMC6318798. (Year: 2015).*

Utani K, Kohno Y, Okamoto A, Shimizu N. Emergence of micronuclei and their effects on the fate of cells under replication stress. PLoS One. Apr. 8, 2010;5(4):e10089. doi: 10.1371/journal.pone.0010089. PMID: 20386692; PMCID: PMC2851613. (Year: 2010).*

Pretreatment of Chromosome Slides for FISH/CGH/SKY Section of Cancer Genomics, Genetics Branch, NCI National Institutes of Health; Published 2005 (Year: 2005).*

Madian et al. (Madian et al., "Analysis of human chromosome classification using centromere position." Measurement 47 (2014): 287-295.) (Year: 2014).*

Russo A, Priante G, Tommasi Am. Prins localization of centromeres and telomeres in micronuclei indicates that in mouse splenocytes chromatid non-disjunction is a major mechanism of aneuploidy. Mutat Res. Dec. 1996;372(2): 173-80. doi: 10.1016/ s0027-5107(96)00137-6. PMID: 9015136. (Year: 1996).*

Maciejowski J, Li Y, Bosco N, Campbell PJ, de Lange T. Chromothripsis and Kataegis Induced by Telomere Crisis. Cell. Dec. 17, 2015;163(7):1641-54. doi: 10.1016/j.cell.2015.11.054. PMID: 26687355; PMCID: PMC4687025. (Year: 2015).*

Muehlbauer et al. Measuring the mitotic index in chemically-treated human lymphocyte cultures by flow cytometry. Mutat Res. Jun. 6, 2003;537(2):117-30. doi: 10.1016/s1383-5718(03)00076-7. PMID: 12787817 (Year: 2003).*

Jung-Min et al. (2011) Sequential administration of camptothecin sensitizes human colon cancer HCT116 cells to paclitaxel via p21Cip1/WAF1 , Animal Cells and Systems, 15:1, 9-17, DOI: 10. 1080/19768354.2011.555187 (Year: 2011).*

Karachristou et al. Triage biodosimetry using centromeric/telomeric PNA probes and Giemsa staining to score dicentrics or excess fragments in non-stimulated lymphocyte prematurely condensed chromosomes. Mutat Res Genet Toxicol Environ Mutagen. 2015 .; cited as NPL document on IDF filed Mar. 28, 2021 (Year: 2015).*

De Jong et al., "Chromosome preparations from microplate cultures of man, dog, rat, and mouse." Human Genetics 33 (1976): 295-298. (Year: 1976).*

Thermo Scientific Plate Guide (BRLSPPLATES/74059 0709; Published 2009 ; Thermo Fisher Scientific Inc.) (Year: 2009).*

International Search Report (with English translation) and Written Opinion (with Machine translation) issued on Dec. 5, 2019 in corresponding International Application No. PCT/EP2019/074870; 11 pages.

Joanna Karachristou et al., "Triage biodosimetry using centromeric/telomeric PNA probes and Giemsa staining to score dicentrics or excess fragments in non-stimulated lymphocyte prematurely condensed chromosomes", Mutation Research. Genetic Toxicology and Environmental Mutagenesis, NL, vol. 793, Nov. 6, 2015, pp. 107-114.

Demetre Zafiropoulos et al., "Biological dosimetry of ionizing radiation: Evaluation of the dose with cytogenetic methodologies by the construction of calibration curves", International Journal of Modern Physics: Conference Series, vol. 44, Sep. 1, 2016, pp. 1660239 1-18.

Radhia M'Kacher et al., "Detection and Automated Scoring of Dicentric Chromosomes in Nonstimulated Lymphocyte Prematurely Condensed Chromosomes After Telomere and Centromere Staining", International Journal of Radiation: Oncology Biology Physics., USA, vol. 91, No. 3, Mar. 1, 2015, pp. 640-649.

* cited by examiner

HIGH-THROUGHPUT METHOD FOR DETECTING CHROMOSOMAL ABERRATIONS AND/OR TELOMERE ABERRATIONS

FIELD

The present application relates to a high-throughput method for detecting chromosomal aberrations and/or telomere aberrations.

BACKGROUND

Over the last decade, numerous research studies have demonstrated the major role of telomeres in genome integrity and stability. With each cell division, the telomeres making up the end of each chromosome shorten. When telomeres become too short, and before genes are affected or chromosomes fuse together, the cell stops dividing and enters senescence. Telomeres are therefore considered to be a biological clock that governs cell ageing. It is now well documented that telomere length is an important biomarker for age-related diseases such as cancer and atherosclerotic cardiovascular disease. [Hubert J et al, Circ Res. 16; 122 (4): 616-623 2018; Staerk L et al, J Am Heart Assoc. 2017 Nov. 14; 6 (11)].

The determination of telomere length and chromosomal aberrations not only has practical implications for clinicians in the therapeutic management of patients but also opens up new fields of research and applications in clinical research, and in particular during therapeutic assays.

The study of telomere length is therefore crucial for the understanding of cellular mechanisms and the assessment and management of patients. To date, several analysis techniques exist.

Terminal restriction fragmentation (TRF) analysis is the first method developed to determine telomere length. It is often considered the reference method. The method allows the estimation of the mean number of terminal repeats carried by all chromosomes. The procedure consists of the digestion of genomic DNA with one or more restriction enzymes. The fragments are then separated by electrophoresis according to their size. The size of the terminal fragments is estimated by comparison with fragments having a known length. [Allshire, Dempster & Hastie, Nucleic Acids Res. 1989 Jun. 26; 17 (12): 4611-27]. The drawback of this method is that it is time-consuming and tedious and requires large amounts of DNA (>1 µg). In addition, it leads to a mean length value and not to individual evidence of telomere shortening or absence.

The quantitative PCR technique, for example MMqPCR, aTL qPCR, has been developed to overcome the obstacle of using large amounts of DNA. However, one of the main drawbacks of this method is that large variations in measurements are observed between different aliquots. In addition, as with the TRF method, the measured values are a mean.

The Q-FISH (Fluorescence in-situ hybridisation) method, possibly combined with flow cytometry, allows the visualization of telomeres by hybridisation using a fluorescence probe on metaphases. [Lansdorp et al. Hum Mol Genet. 1996 May; 5 (5): 685-91]. The advantage of this technique is that it allows the size of each of the 184 human telomeres to be estimated individually and is not limited to a mean or to small telomeres. However, the metaphase quantification method was very laborious to implement and the lengths are expressed in relative fluorescence units.

In 2007, Maria Blasco's team [Canela et al. Proc Natl Acad Sci USA. 2007 Mar. 27; 104 (13): 5300-5] described a new technique based on Q-FISH but on interphase nuclei using the 63× magnification objective in the overall quantification of telomeres and a 96-well plate for cell cultures and hybridisations. However, this technique does not allow the quantification of telomeres of each chromosome or the detection of telomeric aberrations. Moreover, the technique used by Maria Blasco's team is still time-consuming and laborious, as it only allows the analysis of about 1000 cells in 2 hours.

Ioanna Karachriston et al (Mutation Research 793 (2015) 107-114) describe the use of the "premature chromosome condensation (PCC)" technique by fusing human lymphocytes in GO with CHO (Chinese Hamster Ovary) cells in mitosis using a mitogen associated with the labeling of telomeres and centromeres for counting chromosomal aberrations without resorting to the cell culture phase.

This technique is very difficult to introduce in clinical routine and does not allow the quantification of telomeres in human lymphocytes because the sample also contains CHO chromosomes with a telomere size very different from that in human lymphocytes.

Furthermore, this paper does not teach nor suggest overall quantification of telomere size by observing the total fluorescence intensity of interphase nuclei.

Zafiroponlous et al. (Int. J. Mod. Phys. Conf. Ser. 2016.44) also describe the use of the "premature chromosome condensation (PCC)" technique associated with telomere and centromere labeling for counting chromosomal aberrations in the context of biological triage dosimetry after accidental irradiation and the need to have the absorbed dose as soon as possible.

This document does not describe nor suggest the overall quantification of telomeres by observing the total fluorescence intensity of interphase nuclei.

WO 97/014026 describes the Q-FISH technique which consists in quantifying the fluorescence intensity of telomeres in metaphase cells after labeling of telomeres and centromeres with PNA probes.

CN 108 004 299 describes a Q-FISH method that uses genomic DNA instead of cytogenetically fixed cells (see paragraphs [0001], [0012], in this document). This document also describes a telomere-specific PNA probe having a particular sequence. This document does not describe a centromere probe.

Regarding the detection of chromosomal aberrations, homogeneous chromosome labeling remains the most widely used conventional technique in clinical cytogenetics (chromosome classification) as well as in genetic toxicology or biological dosimetry. However, this technique is highly time-consuming and requires highly qualified personnel. Indeed, this technique is based on blood sampling from a heparin-lithium tube of at least 5 mL. This procedure requires the patient to go to the sampling room or to a medical analysis laboratory.

Cytogenetic approaches, combined with in situ hybridisation with DNA probes directed against a whole chromosome or a specific gene, remain the most sensitive and reliable approaches in the diagnosis of patients but also in studies of the clastogenic effects of chemicals. However, this technique is expensive due to the cost of DNA probes and the hybridisation time.

In addition, genomic approaches (Transcriptome, CGH-array, SNP, NGS) have been proposed as an alternative in the detection of genome alterations. However, these techniques, like other genomic approaches, lose their sensitivity when the genome alterations affect repeat sequences (telomeric and centromeric sequences).

Therefore, there is still a need to develop a high-throughput method to detect genome aberrations affecting both single and repeat sequences using a very small number of cells.

SUMMARY

One object of the present invention is to provide a high throughput method for detecting both chromosomal aberrations and telomere aberrations using a biological sample of 150 µL to 200 µL, said method comprising:
- preparing a cytogenetic slide from said sample in a microplate, the mitotic index in said cytogenetic slide being 3 times higher on average than that of the conventional procedure of culturing cells in flasks with 10 to 20 mL of medium,
- simultaneously labeling the telomeres and centromeres with peptide nucleic acid probes with a hybridisation time of 30 minutes to 1.5 hours.
- flow image quantifying the telomere fluorescence intensity on interphase nuclei using a 10× magnification objective for overall quantification of telomeres,
- optionally, quantifying the micronuclei and anaphase bridges using a 10× or 40× magnification objective, and
- automatically capturing the metaphase chromosomes to detect chromosomal aberrations and/or telomere aberrations of each chromosome using a 63× magnification objective.

By "chromosomal aberration" it is meant an abnormality in the number or structure of a chromosome leading to an alteration of the karyotype. Examples of structural chromosomal aberrations include dicentric chromosome, centric rings, acentric chromosomes, chromosomal translocations, isochromosome, insertions and deletions. By way of example of a chromosome number abnormality, supernumerary chromosomes can be mentioned.

The method of the invention also makes it possible to detect micronuclei and anaphase bridges, which are part of the chromosome aberrations.

By micronuclei it is meant chromosome fragments or entire chromosomes expelled from the cell nucleus during mitosis and forming small, well individualised entities in the cytoplasm of interphase cells.

By "anaphase bridge" it is meant DNA in the form of filaments between two daughter cells with or without a telomeric and centromeric sequence, an anaphase bridge indicates the presence of a dicentric chromosome which is an important marker for chromosomal instability or exposure to a genotoxic agent.

By "telomere aberrations" it is meant aberrations affecting the region containing the telomere repeat sequence that is located in the terminal regions of chromosomes. Examples of telomere aberrations include the loss of one telomere, the loss of two telomeres from the same arm (deletion) and the formation of telomere splits.

By "mitotic index" it is meant the ratio of cells in mitosis, in a given cell sample, to the total number of cells.

The mitotic index reflects the rate of cell division.

By "mitotic index in said cytogenetic slide being 3 times higher on average than that of the conventional procedure" it is meant the mitotic index measured in a cytogenetic slide of the present invention prepared according to the method described hereinafter being 3 times higher on average than that obtained by a conventional method in the same sample from the same subject and carried out by the same practitioner with the same equipment.

By "overall telomere quantification" it is meant the quantification from images of the fluorescence intensity of telomeres on interphase nuclei obtained with a 10× magnification objective, to obtain the data consisting of:
- mean telomere size and median telomere size,
- frequency of cells with short telomeres,
- statistical distributions in order to determine intercellular and interindividual heterogeneities,
- biological age of the sample calculated from a standard curve of healthy donors.

Raw telomere fluorescence intensities on interphase nuclei are normalised to those obtained on control slides and converted to kilobase using a standard curve.

Overall quantification of telomeres is performed by specific software to obtain the aforesaid data (TeloScore).

By "automatically capturing the metaphase chromosomes" it is meant the automatic image-based quantification of the fluorescence intensity of telomeres and centromeres of metaphase chromosomes to obtain data consisting in:
- identifying each chromosome from its size, said size being defined by the distance between the telomeres of the short arm (p) and those of the long arm (q) of the chromosome as well as by the ratio between the size of the p part and the q part of the chromosome (centromeric index),
- quantifying the number of centromeres, in order to analyse only complete metaphases,
- quantifying the signal of each telomere of each metaphase chromosome, that is 4 signals per chromosome and 184 signals expected per diploid metaphase).

This automatic capture allows:
- the classification of chromosomes
- the detection of telomere losses and deletions of each chromosome;
- the detection of structural chromosome aberrations such as dicentric chromosomes, centric rings, acentric rings and different types of acentric chromosomes;
- for the detection of simple chromosomal rearrangements, DAPI banding, similar to GTG banding, completes the identification of chromosomes
- for the detection of complex rearrangements, M-FISH type labeling, carried out on the same metaphases, allows the production of a multicolour karyotype which makes the analysis more reliable and sensitive.

The automatic analysis of metaphase chromosomes is performed by a specific software (ChromoScore).

The present invention is implemented by virtue of the development of the following techniques:
- the preparation of a cytogenetic slide in which the proportion of cells in metaphase is higher than in a conventional cytogenetic slide;
- the development of a method for labeling telomeres and centromeres that significantly reduces the labeling time in comparison with a conventional technique requiring 4-6 hours of work,
- the use of a 10× magnification microscopic objective that allows overall quantification of telomeres in 10,000 interphase cells in less than 2 minutes,
- the automatic capture of metaphases allowing successive labeling operations to be made on the same metaphases but also automation in counting of telomeric or chromosomal aberrations.
- the automatic detection of micronuclei and anaphase bridges on mononucleate cells on a same cytogenetic slide.

The present method has several technical advantages over existing methods.

Firstly, the method of the invention is performed with a very small amount of cells. For example, it is sufficient to use only 150 μL to 200 μL of whole blood, that is a quantity of blood that can be obtained by pricking the index finger using the same principle as blood glucose measurement. This reduction in sample volume makes it easier to collect the sample and saves considerable time and reagent consumption.

Secondly, against all expectations, it is observed for the first time by the Inventor that the area/volume ratio of a culture container can influence the mitotic index and that the area/volume ratio of a microplate well is particularly favourable to increase this index and to have very rich and easy to analyse cultures. The use of a microplate for sample culture not only reduces the amount of sample required and the culture time, but also allows the preparation of a cytogenetic slide with a higher mitotic index than that of a conventional cytogenetic slide, which allows, on the one hand, a more reliable cytogenetic study and, on the other hand, the simultaneous labeling of telomeres and centromeres on interphase and metaphase cells.

This approach makes it possible to rapidly provide both information relating to the overall quantification of telomeres on interphase nuclei but also information on each chromosome in order to detect chromosomal aberrations and telomere aberrations using metaphases. The method of the present invention makes it possible, on the one hand, to establish a relationship between the size of telomeres and the frequency of chromosomal aberrations on the same slide, but also to carry out the classification of chromosomes (karyotype) from the metaphase chromosomes and to search for a possible genetic mutation. It also allows the detection of anaphase bridges indicating the presence of a dicentric chromosome which is an important marker for chromosomal instability or exposure to a genotoxic agent.

Preparation of a Cytogenetic Slide

By "cytogenetic slide" it is meant a transparent slide, such as a glass slide, suitable for observation by microscopy, on which the cells to be analysed are laid out and fixed in metaphase and interphase. The mitotic index, which gives us an idea of the richness of the slide in metaphase, has been calculated by the present invention and by the conventional cytogenetic method on the same samples. The mitotic index ratio is between 1.5 and 4 between a cytogenetic slide prepared by the present invention and one prepared by the conventional cytogenetic technique.

In a sample prepared according to a conventional method, a suspension culture of cells is performed in a container with a volume of 10 to 20 mL.

The increase in the mitotic index is correlated with the increase in the proportion of cells in metaphase.

Since metaphase chromosomes are more condensed and visible, the qualitative and quantitative increase in the proportion of metaphase chromosomes not only improves the detection of chromosome aberrations but also automates counting of chromosome aberrations.

Within the scope of the invention, by "biological samples" it is meant preparations of biological fluids or tissues from an animal containing cells to be analysed. Preferably these are blood samples, amniotic fluid in the case of prenatal diagnosis or bone marrow for haematological malignancies. Preferably, the animal is a mammal, and more preferably a human, regardless of sex or age. It may be an embryo, a foetus, a neonate, a child, an adolescent, or an adult.

In one advantageous embodiment, said biological sample is a whole blood sample, marrow, or tissue cell sample.

Said whole blood sample can be obtained using the same principle as obtaining a few drops of blood for blood glucose measurement.

Said tissue cell sample can be obtained from a tissue fragment of tumour or non-tumour nature that may be taken from a patient by biopsy. Said tissue cell sample can be a primary culture or a secondary culture.

According to one embodiment of the method of the present invention, the step of preparing the cytogenetic slide comprises:

culturing the cells in a microplate well, the ratio of the amount of culture medium to the surface area of the well being from 1 mL/cm$^2$ to 1.5 mL/cm$^2$.

More particularly, said microplate may be a 24-well microplate, the working volume of each well of which is 0.5 mL to 1.5 mL.

The cytogenetic slide prepared from this culture has a mitotic index 3 times higher than a slide prepared by a conventional method performed by the same practitioner using the same initial biological sample and the same experimental equipment.

The cell culture can be performed with a conventional liquid culture medium for 72 hours. Said culture medium can be RPMI1640 medium. After culture, the cells are treated with a mitotic spindle inhibitor, for example colchicine, to block the cell cycle of metaphase chromosomes.

The cells then undergo a hypotonic shock which causes the cells to swell due to osmotic pressure difference.

The cell constituents are then fixed by virtue of a fixative, for example an acetic acid/methanol mixture. The volume ratio between acetic acid and methanol in such a mixture can be 1V/3V.

The aforesaid cell treatments can be carried out directly in a microplate well.

Labeling Method

In one advantageous embodiment of the method of the present invention, simultaneous labeling of telomeres and centromeres with peptide nucleic acid probes comprises:

a single step of treating a cytogenetic slide for 1-3 minutes, in particular 2 minutes, with a 3-5% formaldehyde solution, in particular a 4% solution.

In contrast to a conventional method which requires multiple formaldehyde fixation steps, the method of the present invention requires a single formaldehyde solution treatment step.

This treatment enables the three-dimensional structure of the chromosomes to be fixed.

In one more advantageous embodiment of the method of the present invention, the simultaneous labeling of telomeres and centromeres with peptide nucleic acid probes further comprises, after the formaldehyde treatment step, a single step of treating the cytogenetic slide with pepsin for 3-5 minutes, in particular 4 minutes, by immersing a cytogenetic slide previously treated with formaldehyde in a pepsin solution at a concentration of 0.1-0.2 μg/mL.

The pepsin treatment hydrolyses the nuclear proteins and promotes probe access.

In one more advantageous embodiment of the method of the present invention, simultaneous labeling of telomeres and centromeres further comprises, after the pepsin treatment step, the following steps of:

dehydrating the cytogenetic slide successively for 1 minute with a 50% aqueous ethanol solution, a 70% aqueous ethanol solution and pure ethanol, denaturing the chromosomal DNA present on the aforesaid cytogenetic slide obtained at the end of the previous step and denaturing the peptide nucleic acid probes for telomeres and centromeres, hybridising for 10-30 minutes, in particular 20 minutes, at room temperature, between the denatured chromosomal DNA and the denatured peptide nucleic acid probes obtained in the previous step, successively washing said cytogenetic slide after hybridisation.

In one particularly advantageous embodiment of the method of the present invention, the simultaneous labeling of telomeres and centromeres with peptide nucleic acid probes comprises or consists of the following steps of:

treating a cytogenetic slide for 1-3 minutes, in particular 2 minutes, with a 3-5% formaldehyde solution, in particular a 4% formaldehyde solution, treating the cytogenetic slide obtained at the end of the previous step with pepsin for 3-5 minutes, in particular 4 minutes, by immersing said cytogenetic slide in a pepsin solution at a concentration of 0.1-0.2 µg/mL, dehydrating the cytogenetic slide obtained at the end of the previous step successively for 1 minute with a 50% aqueous ethanol solution, a 70% aqueous ethanol solution and pure ethanol, denaturing the chromosomal DNA present on the cytogenetic slide obtained at the end of the previous step and denaturing the peptide nucleic acid probes for telomeres and centromeres, hybridising for 10-30 minutes, in particular 20 minutes, at room temperature, between the denatured chromosomal DNA and the denatured peptide nucleic acid probes obtained in the previous step, successively washing said cytogenetic slide obtained at the end of the previous step.

In comparison with the conventional technique, which requires a day's work, the simultaneous labeling of telomeres and centromeres with the method of the present invention can be carried out in 1 hour while keeping a signal intensity comparable with that obtained by the conventional technique.

By "peptide nucleic acid probe", it is meant an artificial oligomer similar to a DNA or RNA molecule, the backbone of which is comprised of a repetition of N-(2-aminoethyl)-glycine units linked by a peptide bond, the purine and pyrimidine bases being attached to the backbone by methylcarbonyl bonds. Said probe has 5 to 30 nucleic bases.

The sequences of the peptide nucleic acid probes are complementary to the repeat sequence in the telomeric region or the repeat sequence in the centromeric region, respectively. Therefore, the peptide nucleic acid probes hybridise with the telomeres or centromeres at these regions.

Peptide nucleic acid probes are labelled with a fluorochrome, such as cyanine 3 derivatives, rhodamine derivatives or fluorescein derivatives respectively. The density of the fluorescence emitted by the peptide nucleic acid probes hybridising to telomeres can therefore be used to quantify telomere length.

The labeling step of the present invention allows the labeling of telomeres and centromeres with a very strong signal in a hybridisation time of 30 minutes to 1.5 hours. Simultaneous labeling of telomeres and centromeres allows a chromosome to be quickly defined by its centromere and the chromosome territory by the telomeres, which will make chromosome aberration counting and chromosome classification more reliable and robust and independent of the person who analyses.

In one particular embodiment of the method of the present invention, a first peptide nucleic acid probe labels telomeres and a 2nd peptide nucleic acid probe labels centromeres, the first probe and the 2nd probe emitting distinctive fluorescence, respectively.

The sequence of the 1st peptide nucleic acid probe is complementary to the repeat sequence in the telomeric region.

The sequence of the 2nd peptide nucleic acid probe is complementary to the repeat sequence in the centromeric region.

Quantification of Telomere Size by Image Flow

In contrast to the quantification of the fluorescent signal in cytogenetics, which has always been performed with the 63× magnification microscopic objective, the present procedure uses a 10× magnification objective for the overall quantification of telomeres by observing the total fluorescence intensity of the interphase nuclei, which allows the calculation of the mean and median size of the telomeres as well as the heterogeneity in the sample. The observation is performed with a 10× magnification objective for a large field of view and a depth of field at least equivalent to the thickness of the sample. This allows a large number of cells to be analysed while keeping accuracy and sensitivity and avoiding problems of saturation in the capture of a fluorescent signal. The speed of the acquisition and analysis system makes this measurement particularly interesting. With this technique, 10,000 cells can be analysed in less than 2 minutes. It also provides a histogram of the frequency of telomere length and data on cell morphology (irregularities, roundness, concavity, etc.) as a function of telomere size or the amount of 4',6-diamidino-2-phenylindole (DAPI) used to label the chromosomes. Internal controls may be introduced at each staining. These are two lymphoblastoid lines with well-established cytogenetic and telomere characterisation. The telomere size of these two lines has been measured by several other telomere quantification techniques (TRF, PCR and Flow FISH). These two controls allow us to convert the fluorescence intensity into kilobase units. In addition to this internal control, there is an external control consisting of fluorescent beads with a specific intensity. The purpose of this calibration slide is to check the fluorescence intensity of the capture system, including the fluorescence intensity of the lamp. An adjustment to the fluorescence intensity will be performed before each capture by adjusting several parameters such as the lamp intensity or camera gain (TeloScore).

Detection of Micronuclei and Anaphase Bridges:

The detection of micronuclei and anaphase bridges is performed automatically by fluorescence microscopy using software (BridgeScore) on mononucleate cells. For micronuclei, telomere and centromere labeling is used to determine the nature of these micronuclei. Micronuclei detected with only telomeric sequences correspond to terminal deletions related to exposure to a clastogenic agent. Micronuclei detected with telomeric and centromeric sequences correspond to the removal of an entire chromosome that is related to exposure to an aneugenic agent.

The detection of anaphase bridges relates to the presence of a DNA filament connecting two daughter cells called an anaphase bridge. The length of these bridges is measured as well as the presence or absence of centromeric or telomeric sequences. The presence of telomeric or centromeric sequences in the anaphase bridge shows that the dicentric chromosome is the result of a fusion of two chromosomes with a telomeric dysfunction. The number of cells that are adhered is also automatically searched for and may indicate a specific dicentric chromosome configuration (the two centromeres are very close to each other). In this case, the size of the anaphase bridge is very small and the two daughter cells appear to be adhered as binucleate cells.

Automatically Capturing the Metaphase Chromosomes

The search and capture of metaphases are performed automatically by fluorescence microscopy using software with a well-defined capture integration time.

The different parts of the chromosomes are labelled with different fluorochromes. Chromosomes can be labelled with different fluorochromes, each binding strongly to certain nucleic bases: for example, centromeres are labelled with FITC carried by a centromere-targeted peptide nucleic acid probe, telomeres are labelled with cyanine 3 carried by a telomere-targeted peptide nucleic acid probe and chromosome backbones are labelled with DAPI (4',6-diamidino-2-phenylindole).

This chromosome labeling makes it possible to determine a codification for each chromosome as well as for each aberration and the development of a software program.

Using this specific software, the chromosome backbone, the distance of each telomere from the end of the backbone (distance D), and the distance between each telomere and the centromere (distance d) are calculated. The distances d and D are used to identify pairs of chromosomes from their size and also from the D/d ratio.

Parameters such as number of centromeres, number of telomeres detected per chromosome, number of telomeres detected per cell, sum of fluorescence intensity, mean of fluorescence intensity, median of fluorescence intensity, ratio p/q of intensities are calculated.

This information is used to classify chromosomes and to indicate chromosomal aberrations or telomere aberrations.

The method of the present invention can also be combined with other cytogenetic techniques, such as M-FISH (multiplex fluorescence in situ hybridisation) and NGS (Next-Generation Sequencing)-exome, which allows the study of protein-coding regions of the genome. By way of example, the combination of the method of the present invention with the NGS-exome technique may target only the coding regions of the genome involved in rearrangements detected after labeling of telomeres and centromeres followed by M-FISH staining. This approach allows targeted NGS to be performed.

Another object of the present invention relates to detection kits.

The invention provides a high-throughput detection kit for telomere quantification and detection of chromosomal aberrations and/or telomere aberrations, comprising:
  a ready-to-use solution of peptide nucleic acid probes for telomeres and centromeres,
  wash buffers required for hybridisation,
  standard slides for telomere quantification,
  standard slides to check fluorescence intensity of the microscope.

The standard slides for telomere quantification are reference slides prepared from lymphoblastoid lines derived from healthy subjects. Telomere size was measured by the TRF reference technique to obtain the size in kilobases. These lines include no chromosomal aberrations.

The standard slides to check fluorescence intensity of the microscope are slides with fluorescent beads calibrated with a well-defined intensity.

The present invention also relates to a method for detecting chromosomal aberrations, said method comprising:
  labeling the telomeres and centromeres of metaphase cells with a ready-to-use solution of nucleic acid probes,
  automatically capturing the fluorescent signals of the telomere and centromere labeling,
  analysing the image obtained in the previous step to obtain the data set: counting the number of metaphase centromeres, identifying each chromosome from its size and the ratio between the short arm (p) and the long arm (q), and quantifying the signal of each telomere of each metaphase chromosome, detecting chromosomal structural aberrations such as dicentric chromosomes, centric rings, acentric rings and different types of acentric chromosomes,
  possibly DAPI banding, similar to GTG banding, to complete the identification of chromosomes and detect single translocations,
  optionally M-FISH labeling carried out on the same metaphases, for performing a multicolour karyotype to detect complex rearrangements and makes the analysis more reliable and simpler.

In one embodiment, the metaphase cells are those contained in a cytogenetic slide prepared according to the method of the present invention described above.

The present invention also relates to a method for detecting micronuclei and anaphase bridges, said method comprising:
  (i) labeling telomeres and centromeres of interphase cells with a ready-to-use solution of nucleic acid probes,
  (ii) automatically capturing the fluorescent signals from the telomere and centromere labeling,
  (iii) analysing the image obtained in step (ii) to obtain the data set: total number of micronuclei, number of micronuclei with only telomeric sequences, and number of micronuclei with both telomeric and centromeric sequences,
  (iv) analysing the image obtained in step (ii) to obtain the data set: identification of anaphase bridges by detecting the presence of a DNA filament connecting two daughter cells, length of the bridge, detection of the presence or absence of centromeric or telomeric sequences in the bridge, counting the number of adhered cells (very reduced bridge).

Micronuclei can be identified if there is the presence of telomeric sequences alone, which corresponds to terminal deletions related to exposure to a clastogenic agent, or the simultaneous presence of telomeric and centromeric sequences, which corresponds to the elimination of an entire chromosome that is related to exposure to an aneugenic agent.

The presence of anaphase bridges is correlated with the detection of a DNA filament connecting two daughter cells. The length of these bridges is measured as well as the presence or absence of centromeric or telomeric sequences in the bridge. The presence of these sequences in the anaphase bridge shows that the dicentric chromosome is the result of a fusion of two chromosomes with telomere dysfunction. The number of cells that are adhered is also searched for and may indicate a specific configuration of dicentric chromosomes (the two centromeres are very close to each other).

This method can be performed automatically by fluorescence microscopy using software (BridgeScore).

The present invention is further explained by the following figures and examples.

DETAILED DESCRIPTION

Examples

1. Materials and Methods

Cell Lines

The cell lines tested in the examples are lymphoblastic lines from healthy donors, tumour lines from Hodgkin's lymphoma, Burkitt's lymphoma and mantle cell lymphomas were used.

Q-FISH Assay

The Q-FISH assay, which allows visualisation of telomeres by hybridisation using a fluorescence probe on metaphases, is implemented according to the method described in [Lansdorp et al. Hum Mol Genet. 1996 May; 5 (5): 685-91.]

TRF Assay

The TRF assay is performed according to the technique described in [Kimura et al, Nat Protoc. 2010 September; 5 (9): 1596-607]

qPCR Assay

The qPCR assay is implemented according to the method described in [OCallaghan & Fenech, Clin Nutr. 2012 February; 31 (1): 60-4].

Telomere and Centromere Labeling

A protocol for telomere and centromere labeling is illustrated below.

1. washing the cytogenetic slides in a first phosphate-buffered saline (PBS) 1 solution for 1 minute at room temperature,
2. fixing in 4% formaldehyde solution for 2 minutes at room temperature,
3. washing twice in phosphate-buffered saline (PBS) for 1 minute,
4. treating with pepsin solution (0.1 μg/mL) at 37° C. for 4 minutes,
5. washing twice in phosphate-buffered saline (PBS) for 1 minute,
6. successively dehydrating for 1 minute at 4° C. with 50% aqueous ethanol, 70% aqueous ethanol, pure ethanol
7. drying the slides,
8. denaturing the probes and chromosomal DNA at 80° C. for 3 minutes,
9. Hybridising for 20 minutes at room temperature,
10. washing the cytogenetic slides
11. staining the chromosomes with DAPI and applying a contrast stain.

Chromosome Aberration Analysis

The analysis is performed on metaphase cells after telomere and centromere labeling and automatically capturing telomere and centromere fluorescent signals:

Identification of each chromosome from its size defined by the distance between the telomeres of the short arms (p) and long arms (q) of the chromosome as well as the ratio of the size of the p part to the q part of the chromosome (centromere index).

Quantification of the number of centromeres to analyse complete metaphases only.

Quantification of the signal of each telomere (4 signals per chromosome and 184 signals expected per diploid metaphase).

Detection of telomere losses and deletions on each chromosome.

Detection of structural chromosome aberrations such as dicentric chromosomes, centric rings, acentric rings and different types of acentric chromosomes.

For the detection of simple chromosomal rearrangements, DAPI banding, similar to GTG banding close to that of GTG banding, completes the identification of chromosomes.

For complex chromosomal changes, M-FISH labeling, performed on the same metaphases, allows the production of a multicolour karyotype which makes the analysis more reliable and sensitive.

This software offers a simple interface allowing manual correction of the data and is capable of "learning" over time.

2. Results 2.1 Technical Validation of the Method of the Invention

Validation of the Microplate Culture Approach

Figure 1:
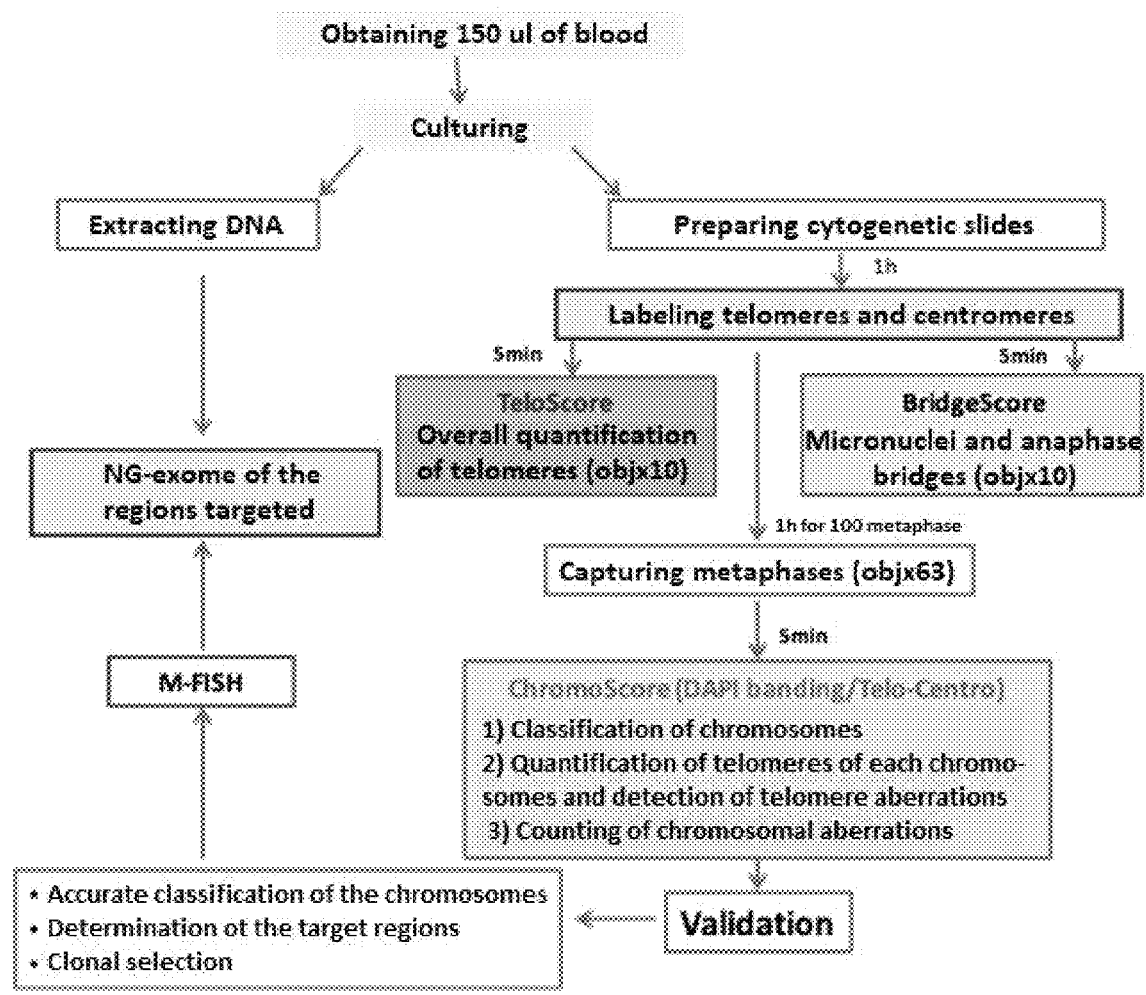
FIG. 1: This figure illustrates a schematic of the high-throughput method for telomere quantification, micronucleus and anaphase bridge detection and chromosome and telomere aberration detection of the present invention.
Figure 2:
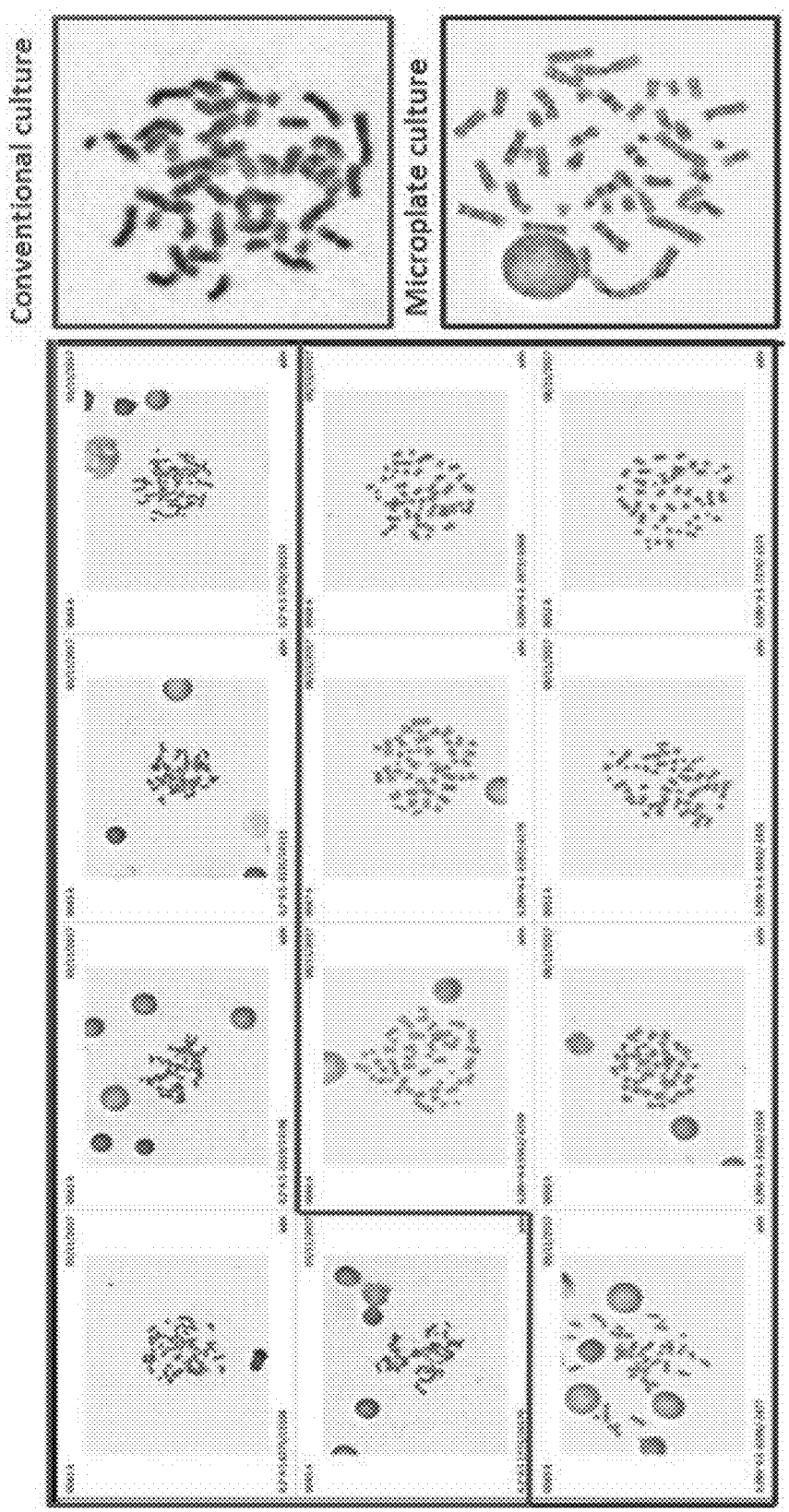
FIG. 2: This figure shows the comparison between the quality and quantity of metaphases obtained by the microplate technique and the conventional technique. Images of metaphases from conventional culture (top frame) and images of metaphases from microplate culture (bottom frame). This comparison was made under the same conditions with the same cell sample.

Microplate cell culture was validated against the conventional technique (25 cm² flask culture) on a cohort of 70 patients with lymphoid diseases, 50 healthy donors and 150 patients with inflammatory or proliferative syndrome. Whole blood from 50 patients and marrow from 20 patients were cultured using both approaches. No culture failures were observed with the microplate technique and with a quality of metaphases allowing reliable and sensitive cytogenetic analysis. In contrast, using the conventional technique, several culture failures were observed (5 out of 20 marrows and 7 whole blood out of 50 cancer patients) with a quality of metaphases that is less interesting and that will not allow an automatic analysis of chromosomal aberrations (FIG. 2).

Interphase Nucleus Capturing with a 10× Magnification Objective

Figure 3A:
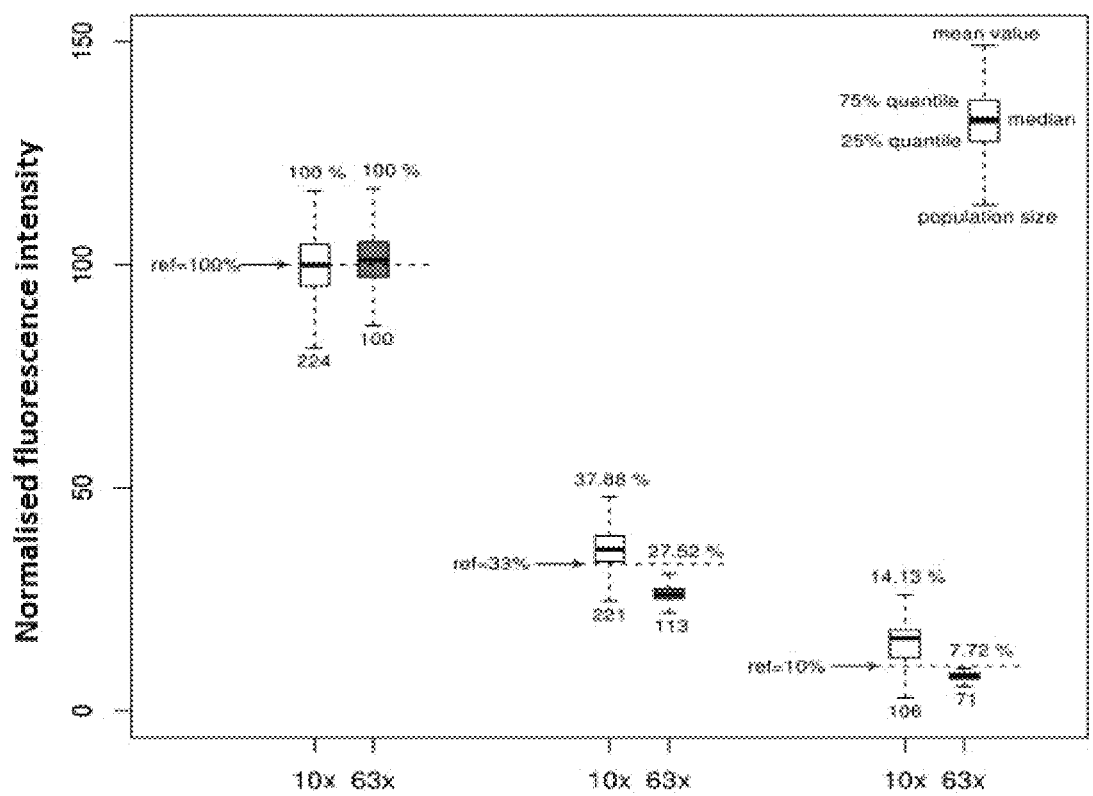
FIG. 3A: This figure shows the comparison of the fluorescence intensity of the 6 μm calibration beads measured by a 10× microscopic objective or a 63× microscopic objective with different intensities (100%, 33% and 10%).
Figure 3B:
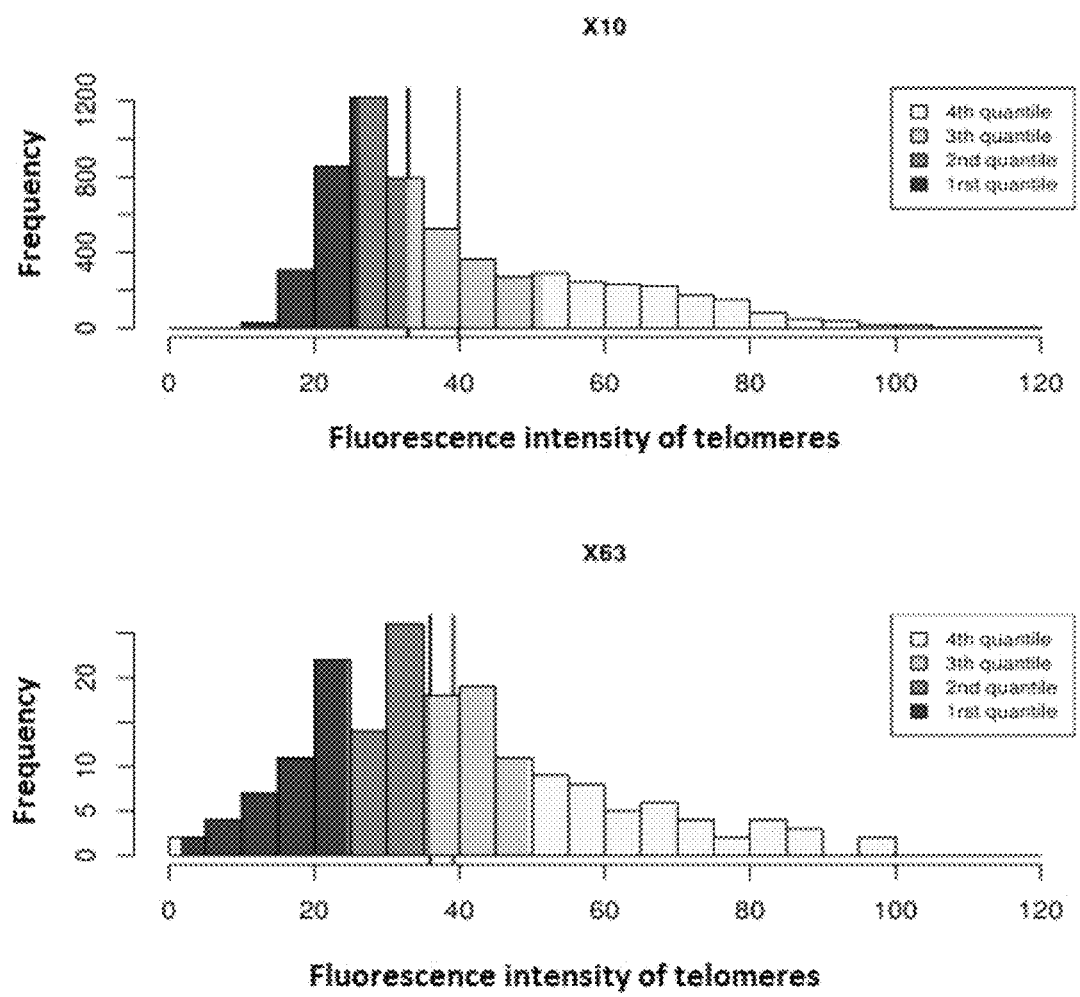
FIG. 3B: This figure shows the distribution of fluorescence intensity of the cells in quartiles measured by a 10× microscope objective or a 63× microscope objective.

The fluorescence capture method with a 10× magnification objective is compared with a method using a 63× magnification objective. Fluorescence intensities emitted by calibrated beads are measured by a 10× and a 63× microscopic objective respectively. The results obtained are comparable (FIGS. 3A and 3B). However, for low fluorescent intensities, the use of the 10× objective allows one to get closer to the exact fluorescence value of the beads.

Figure 4:
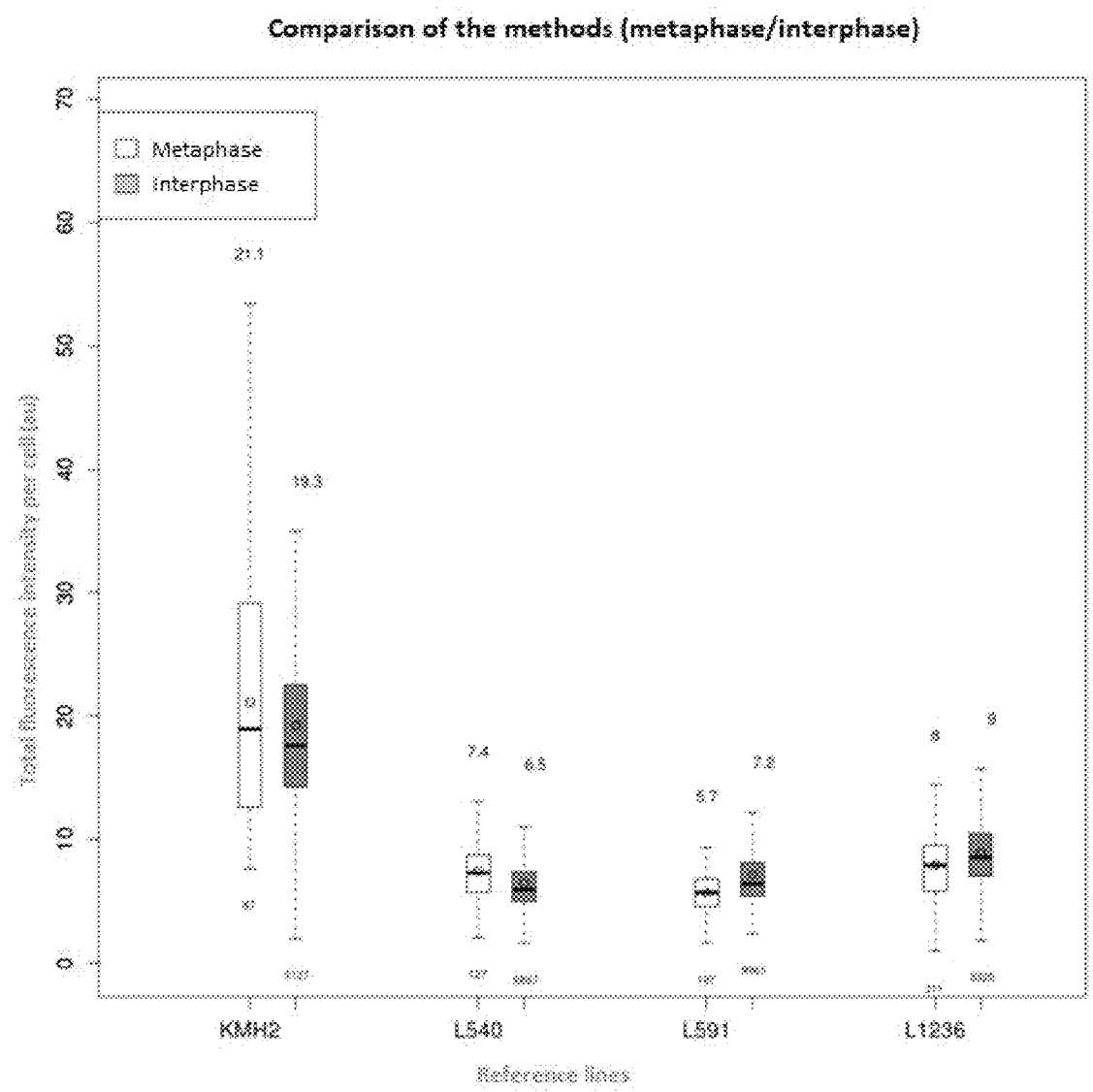
FIG. 4: This figure shows the comparison of telomere quantification on metaphases (Q-FISH) and interphases (present invention) using four cell lines.

The interphase nucleus capture method using a 10× magnification objective and the classical (Q-FISH) metaphase capture method using a 63× magnification objective are also tested on different human cell lines and on circulating lymphocytes from cancer patients. A strong correlation is observed between the fluorescence intensity obtained from metaphases by the Q-FISH method and the fluorescence intensity obtained from interphase nuclei by the method of the present invention (FIG. 4). Telomere size analyses are performed using software for giving the mean size, frequency of cells with short telomeres, and heterogeneity of telomere size.

Telomere Quantification

Figure 5:
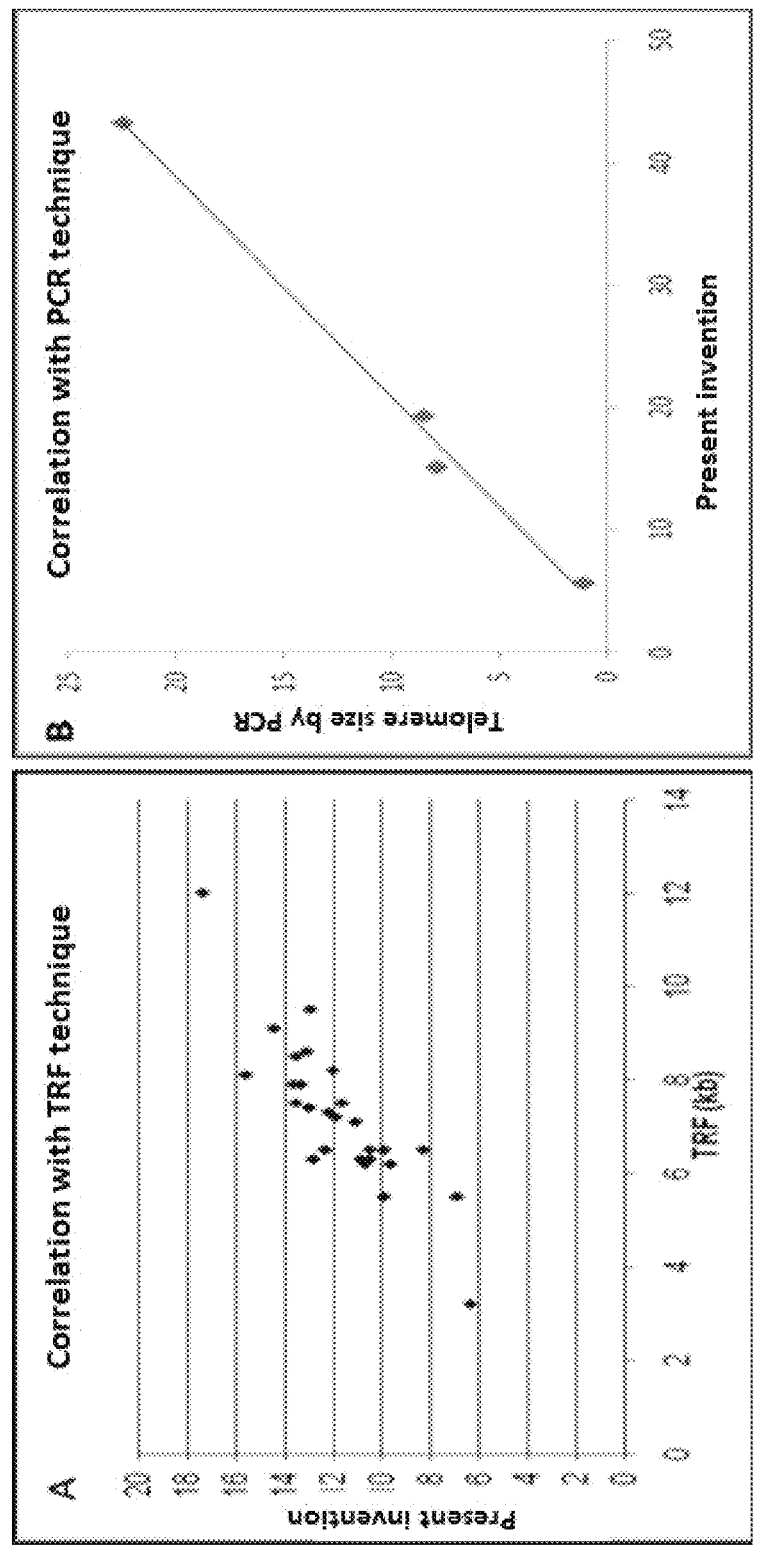
FIG. 5: This figure shows the comparison between the telomere quantification measured by the method of the invention and the result obtained by FISH (A) and the result obtained by PCR (B).

The telomere quantification result obtained by the method of the present invention is also compared with that obtained by the TRF (terminal restricted fragment) technique and that obtained by the PCR technique (FIG. 5). This comparison shows a significant correlation between the method of the present invention and conventional techniques with respect to telomere quantification and thus validates this new approach with respect to the reference technique (TRF) and also with respect to the most currently used technique (PCR).

2.2 Application of the Method of the Invention

Impact of Age on Telomere Size

Figure 6:
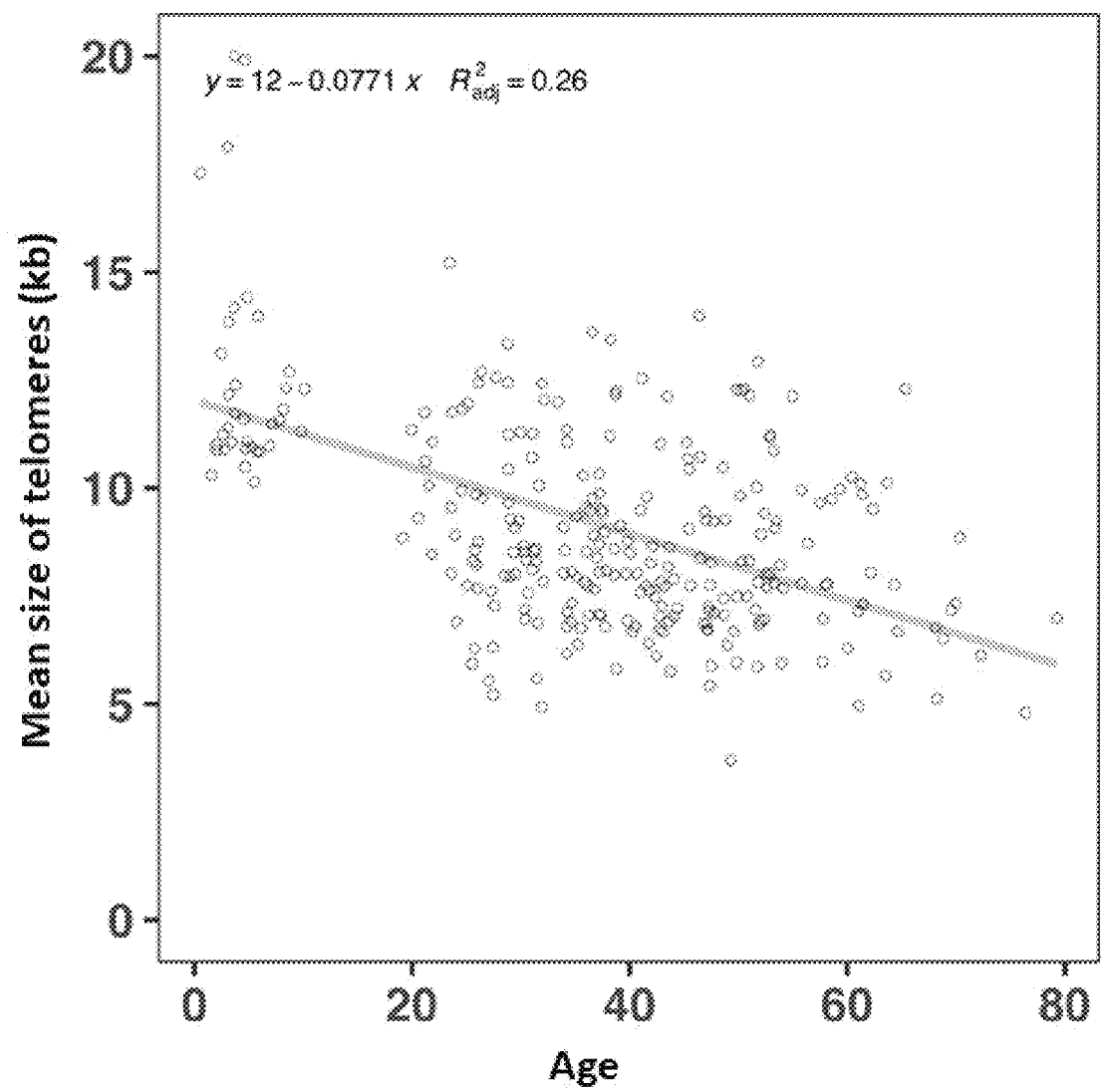
FIG. 6: This figure shows the correlation between the mean telomere size measured by the present invention and age in a cohort of 420 healthy donors. The mean size is expressed in kb.

Telomere sizes in circulating lymphocytes obtained from 420 healthy donors aged between 1 and 80 years were analysed by the method of the invention. The donors are classified into 5 age groups. The total fluorescence intensity of telomeres is quantified. For each sample, more than 10,000 cells were analysed. The result clearly shows a progressive decrease in telomere length with increasing age with a mean loss of 76 bp per year (FIG. 6). This telomere regression mean as a function of age perfectly correlates with the literature (Vera el al. (2012), Cell Rep 2 (4): 732-737.).

Figure 7:
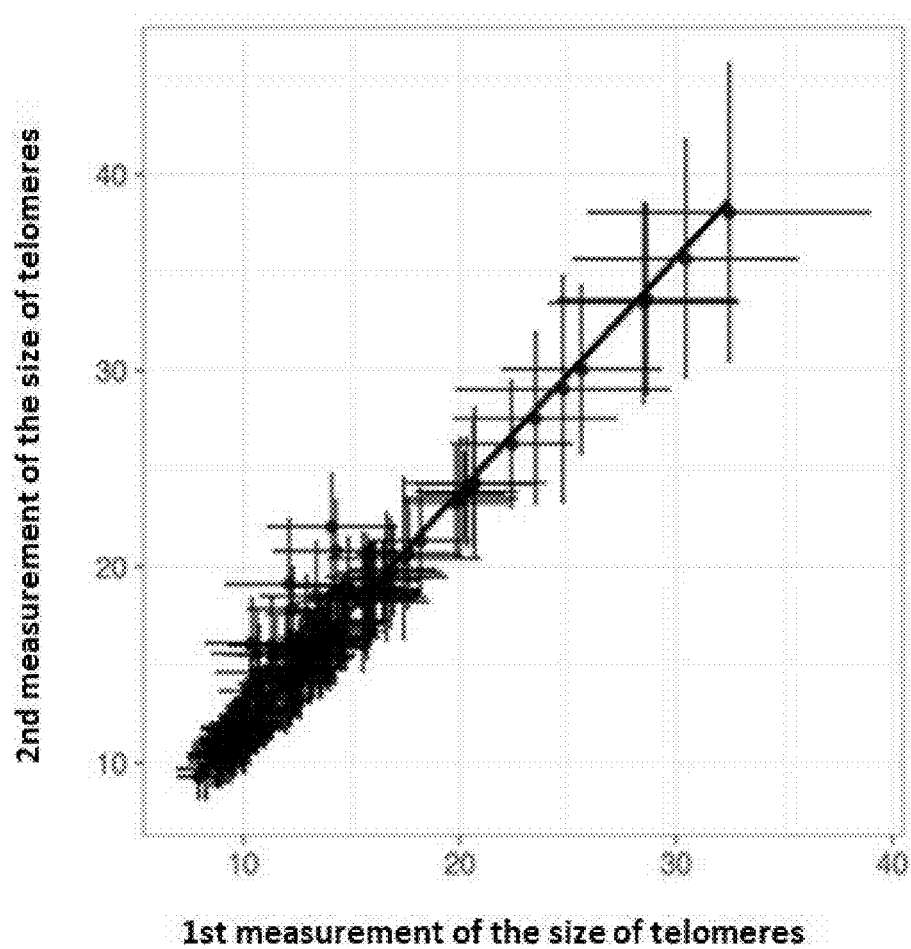
FIG. 7: Reproducibility of the method of the invention with two different measurements of the same sample comprising 420 donors.

Furthermore, the method of the invention gives good reproducibility with two measurements of telomere size from the same population two years apart (FIG. 7).

Frequency of Micronuclei and Anaphase Bridges

Figure 8:
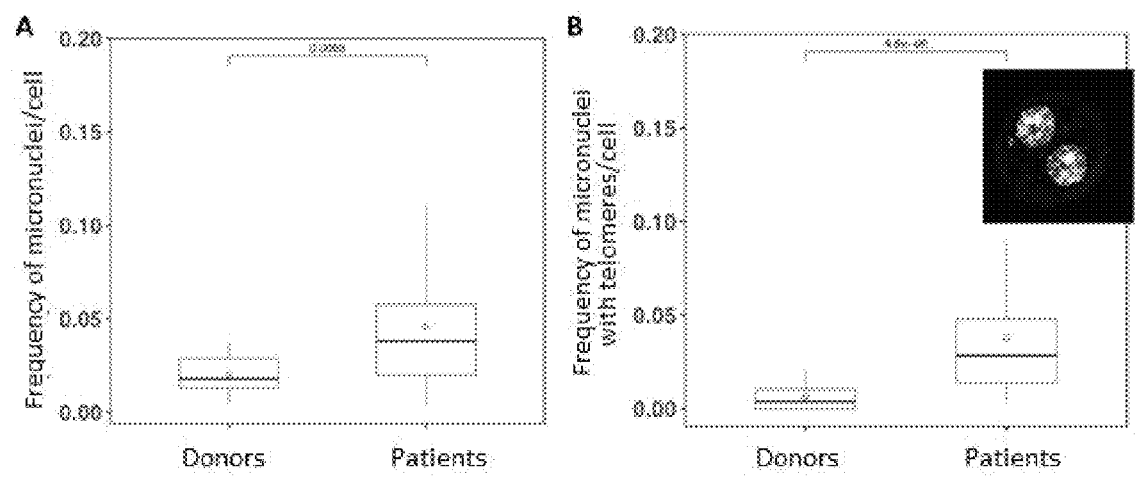
FIG. 8: This figure shows the frequency of micronuclei in healthy donors and cancer patients with (A) the total number of micronuclei. (B) the difference between micronuclei with only telomeric sequences detected by virtue of the present invention between patients and donors.

The frequency of micronuclei and anaphase bridges was evaluated in circulating lymphocytes from healthy donors and cancer patients by the method of the invention. The results obtained show a significant increase in the frequency of micronuclei, mainly micronuclei with only telomeric sequences (FIG. 8). The present invention has made it possible to detect the nature of these micronuclei which is related to genotoxic stress.

Figure 9:
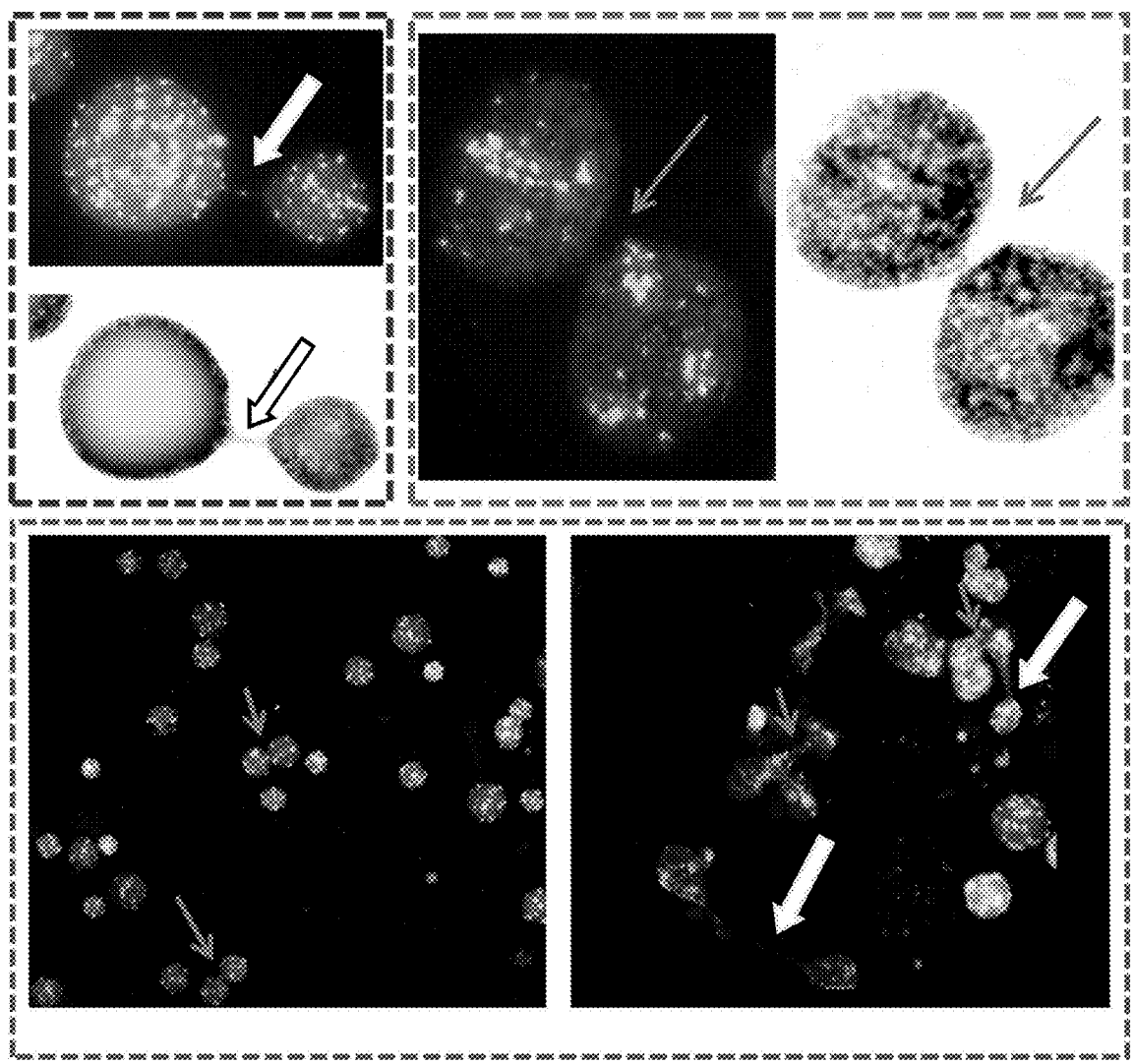
FIG. 9: This figure shows the detection of anaphase bridges in interphase cells from cancer patients. The method of the invention allows quite long anaphase bridges (white arrow) to be distinguished with telomeric and/or centromeric sequences corresponding to the presence of a dicentric chromosome resulting from a fusion of two chromosomes or very reduced anaphase bridges (grey arrow) indicating the presence of a dicentric chromosome with two centromeres very close to each other.

The detection of anaphase bridges was also performed on a large cohort of healthy donors and patients. The detection of the different configurations of anaphase bridges was compared with data obtained by chromosomal aberrations. The method of the invention makes it possible to detect mechanisms involved in the formation of anaphase bridges (FIG. 9). The method of the invention makes it possible to detect long anaphase bridges, easily detectable on cytogenetic slides and which are related to the formation of a dicentric resulting from a fusion of two chromosomes (telomere dysfunction). This procedure also allows the detection of very reduced anaphase bridges which are linked to the presence of a very specific configuration of dicentric chromosomes (the two centromeres very close to each other). These different configurations of anaphase bridges are easily detectable on cytogenetic slides prepared according to the method of the invention described above, allowing very rapid detection of chromosomal instability.

Accuracy in the Detection of Chromosomal Aberrations

Example 1

Figure 10:
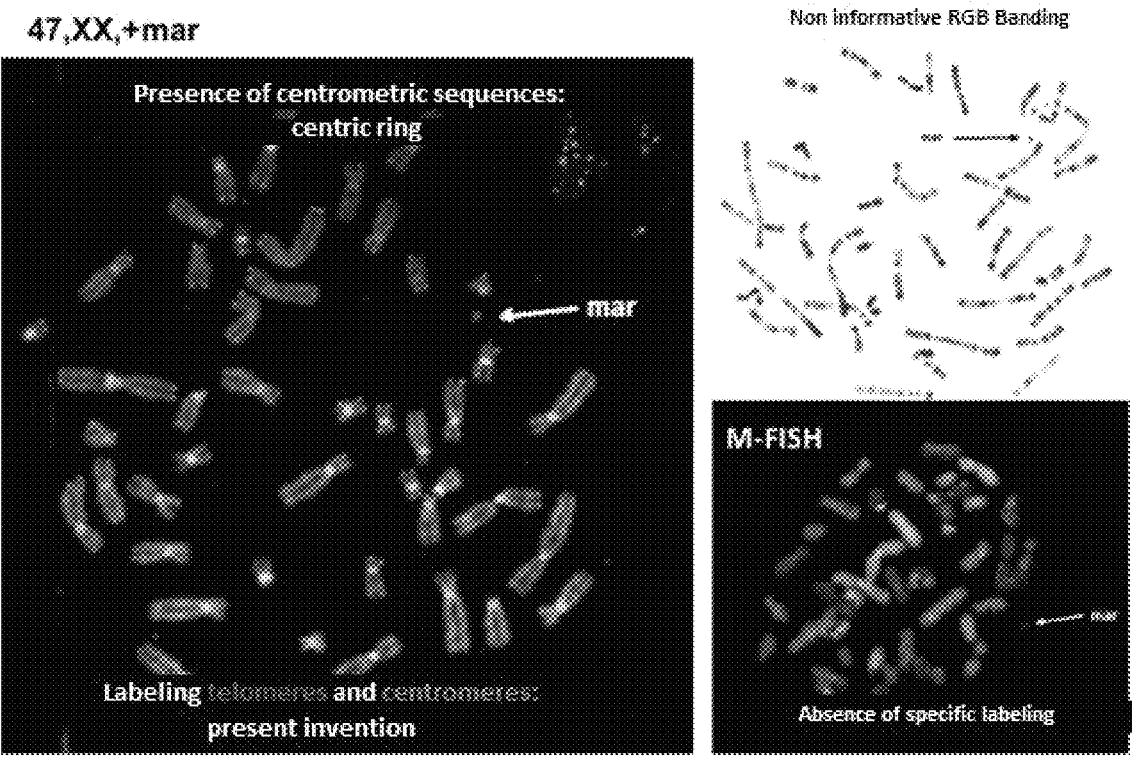
FIG. 10: This figure shows the detection of a supernumerary marker chromosome corresponding to a centric ring in a prenatal sample by the method of the invention. This aberration cannot be detected by the RBG or M-FISH technique alone.

A supernumerary marker chromosome corresponding to a centric ring, essentially consisting of centromeric sequences, can be detected by the method of the invention. The phenotype is infertility. This chromosomal aberration is undetectable by conventional techniques such as molecular cytogenetics or M-FISH alone (FIG. 10). Telomere and centromere labeling allowed centromeric sequences to be seen and the nature of the chromosomal aberration to be defined.

Example 2

In prenatal diagnosis, presence of a translocation t (9; 10) (q34; q26.3) in the father and the fetus, the conventional technique (RBG) as well as molecular cytogenetic techniques (M-Banding and chromosome painting) detect a non-balanced translocation.

Figure 11:
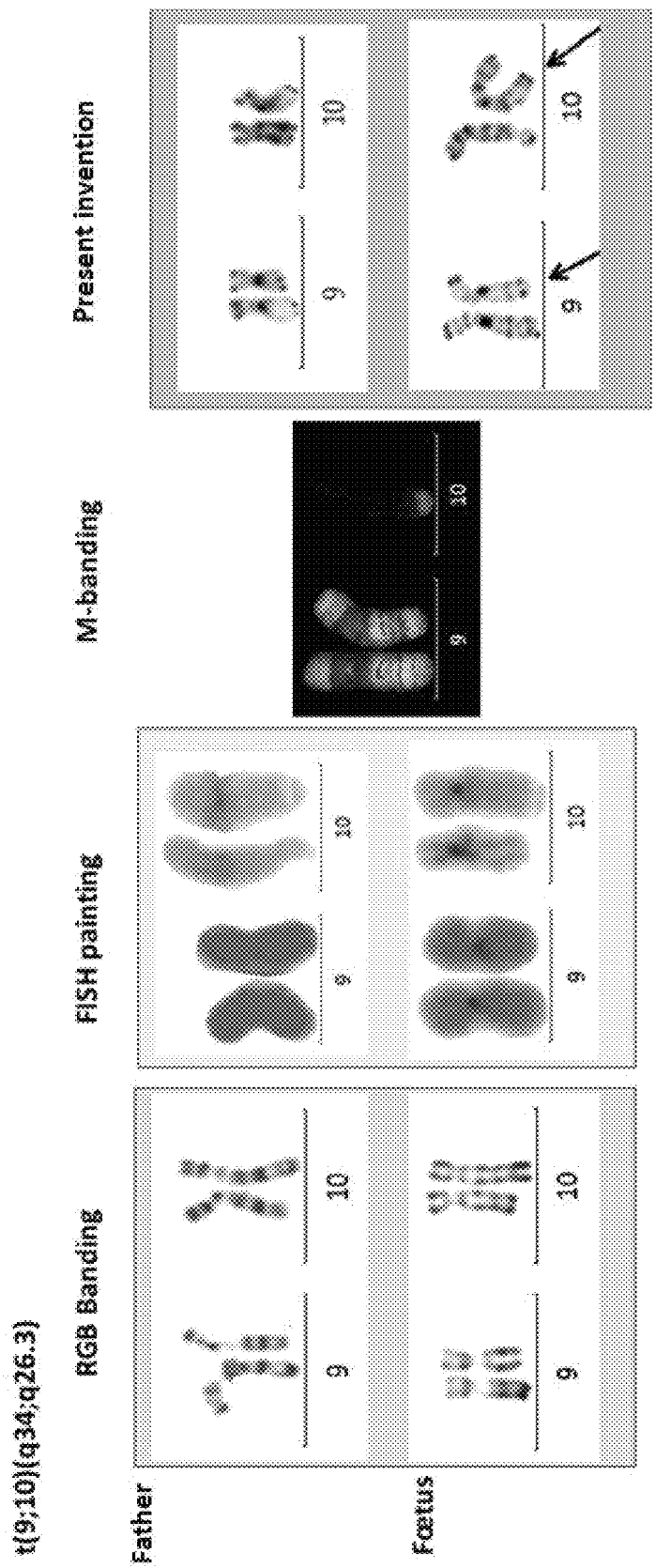
FIG. 11: This figure shows the detection of a chromosomal translocation and the identification of the nature of this translocation by the conventional technique (top figure), by chromosome in situ hybridisation, by M-banding and by the method of the invention (bottom figure) within the scope of a prenatal examination with a decision of genetic counselling to be taken in case the translocation is not balanced. As the translocation affects the telomeric part of chromosome 10q, it has not been detected by conventional or molecular cytogenetics. The present invention allows detection of telomeric sequences and confirmation of the nature of the translocation.

The method of the invention, which leads to labeling of telomeres and centromeres, has made it possible to observe that chromosome 10 has exchanged only the telomeric part with chromosome 9 (FIG. 11). The presence of the telomeric sequences in chromosome 9 showed that this was therefore a balanced translocation. In comparison with conventional techniques, the method of the invention not only allows the detection of the chromosomal aberration, but also more precisely the nature of the aberration.

Example 3

Figure 12:
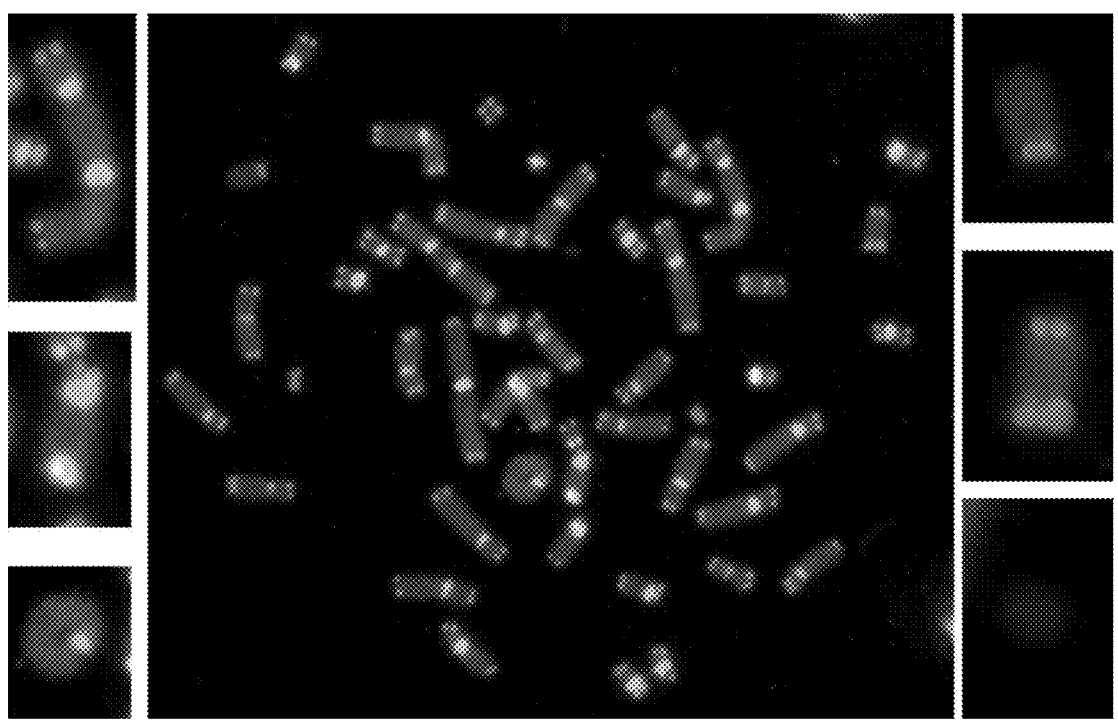
FIG. 12: This figure shows the detection of chromosomal aberrations in metaphase cells after labeling of telomeres and centromeres: dicentric chromosomes, centric rings and acentric chromosomes.

The method of the present invention also makes it possible to detect all chromosomal aberrations induced by a genotoxic agent such as irradiation. The method of the invention allows an evaluation of the number of centromeres, the presence of the dicentric chromosome, translocations, different types of acentric chromosomes resulting from a terminal deletion, interstitial deletion or fusion between two terminal deletions. FIG. 12 shows that the method of the invention makes it possible to detect different configurations of the dicentric chromosome, such as the dicentric with the two linear and well-spaced centromeres, the dicentric with the centromeres identical to the telomeres and the dicentric with the two centromeres very close or identical to each other. This figure shows that the method of the invention can also distinguish between centric and acentric rings and characterise acentric chromosomes, such as acentric ring from a terminal deletion, acentric ring from an interstitial deletion and acentric ring from a fusion between two terminal acentric rings.

Example 4

Figure 13:
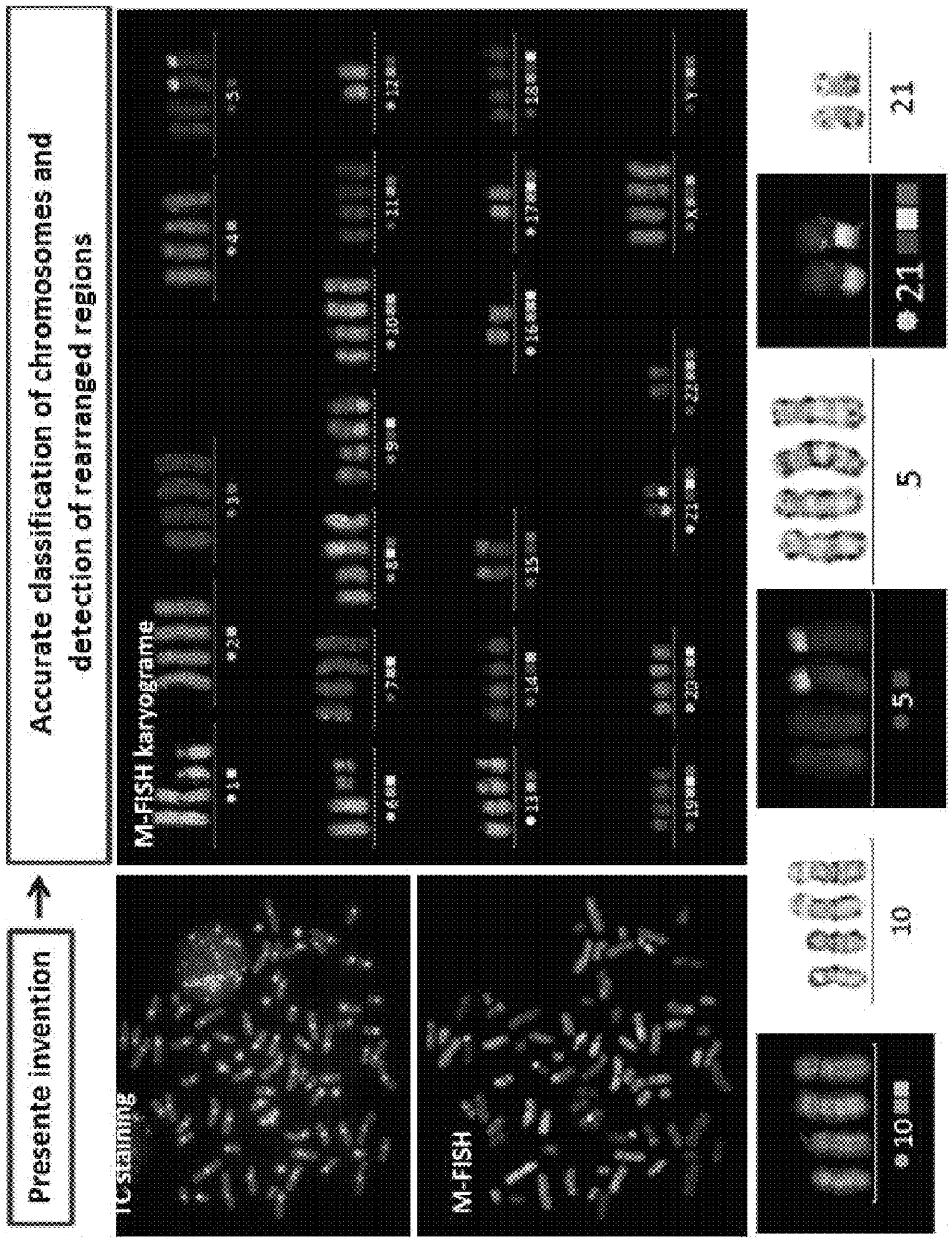
FIG. 13: This figure shows that a sequential analysis after telomere and centromere labeling associated with the M-FISH technique allows a very accurate classification of chromosomes and also a detection of chromosomal aberrations, such as the dicentric chromosome with a very specific configuration, a chromosomal aberration difficult to detect by a conventional technique.

The method of the present invention also allows the detection of a specific configuration of the dicentric chromosome, which configuration is very difficult to detect by conventional techniques. The method of the invention allows a more accurate classification of chromosomes and a more reliable detection of chromosomal aberrations (FIG. 13).

REFERENCES

Benetos A, Toupance S, Gautier S, Labat C, Kimura M, Rossi P M, Settembre N, Hubert J, Frimat L, Bertrand B, Boufi M, Flecher X, Sadoul N, Eschwege P, Kessler M, Tzanetakou I P, Doulamis I P, Konstantopoulos P, Tzani A, Korou M, Gkogkos A, Perreas K, Menenakos E, Samanidis G, Vasiloglou-Gkanis M, Kark J D, Malikov S, Verhulst S, Aviv A. Short Leukocyte Telomere Length Precedes Clinical Expression of Atherosclerosis: The Blood-and-Muscle Model. Circ Res. 2018 Feb. 16; 122 (4): 616-623. doi: 10.1161/CIRCRESAHA.117.311751. Epub 2017 Dec. 14.
Staerk L, Wang B, Lunetta K L, Helm R H, Ko D, Sherer J A, Ellinor P T, Lubitz S A, McManus D D, Vasan R S, Benjamin E J, Trinquart L. Association Between Leukocyte Telomere Length and the Risk of Incident Atrial Fibrillation: The Framingham Heart Study. J Am Heart Assoc. 2017 Nov. 14; 6 (11).
Allshire R C (1), Dempster M, Hastie N D Human telomeres contain at least three types of G-rich repeat distributed non-randomly. Nucleic Acids Res. 1989 Jun. 26; 17 (12): 4611-27.
Canela A, Vera E, Klatt P, Blasco M A. High-throughput telomere length quantification by FISH and its application to human population studies. Proc Natl Acad Sci USA. 2007 Mar. 27; 104 (13): 5300-5. Epub 2007 Mar. 16.
Harley C B (1), Futcher A B, Greider C W. Telomeres shorten during ageing of human fibroblasts. Nature. 1990 May 31; 345 (6274): 458-60.
Kimura M, Stone R C, Hunt S C, Skurnick J, Lu X, Cao X, Harley C B, Aviv A. Measurement of telomere length by the Southern blot analysis of terminal restriction fragment lengths. Nat Protoc. 2010 September; 5 (9): 1596-607.
Cawthon R M. Telomere measurement by quantitative PCR. Nucleic Acids Res. 2002 May 15; 30 (10): e47.
Cawthon R M. Telomere length measurement by a novel monochrome multiplex quantitative PCR method. Nucleic Acids Res. 2009 February; 37 (3): e21.
O'Callaghan N J (1), Toden S, Bird A R, Topping D L, Fenech M, Conlon M A. Colonocyte telomere shortening is greater with dietary red meat than white meat and is attenuated by resistant starch. Clin Nutr. 2012 February; 31 (1): 60-4.
Vera E, Bernardes de Jesus B, Foronda M et al. The rate of increase of short telomeres predicts longevity in mammals. Cell Rep 2012; 2 (4): 732-737.

The invention claimed is:
1. A high throughput method for detecting chromosomal aberrations and/or telomere aberrations using a biological sample comprising cells of 150 µL to 200 µL, comprising:
preparing a cytogenetic slide from said biological sample in a microplate;
simultaneously labelling telomeres and centromeres with peptide nucleic acid probes with a hybridisation time from 10 minutes to 1.5 hours; quantifying a total fluorescence intensity of telomeres on interphase nuclei using a 10× magnification objective for global telomere length quantification and cell morphology assessment; and
automatically capturing metaphase chromosomes to detect chromosomal aberrations and/or telomere aberrations in each chromosome,
wherein the step of preparing the cytogenetic slide comprises:
culturing the cells from the biological sample in a microplate well, a ratio of an amount of a culture medium to a well surface area of which is 1 mL/cm$^2$ to 1.5 mL/cm$^2$.
2. The method according to claim 1, for detecting chromosomal aberrations selected from the group consisting of micronuclei, anaphase bridges, dicentric chromosomes, centric rings, acentric chromosomes, chromosomal translocations, isochromosome, and chromosome insertions and deletions.
3. The method according to claim 1, said method comprising:
preparing a cytogenetic slide from said sample in a microplate;
simultaneously labelling the telomeres and centromeres with peptide nucleic acid probes with a hybridisation time from 30 minutes to 1.5 hours;
flow image quantifying the telomere fluorescence intensity on interphase nuclei using a 10× magnification objective for overall telomere quantification;
quantifying the micronuclei and anaphase bridges using a 10× or 40× magnification objective; and
automatically capturing the metaphase chromosomes to detect chromosomal aberrations and/or telomere aberrations in each chromosome.
4. The method according to claim 1, wherein said biological sample is a whole blood sample, bone marrow, or tissue cell sample.

5. The method according to claim 1, wherein simultaneously labelling the telomeres and centromeres comprises:
a single step of treating a cytogenetic slide for 1 to 3 minutes.

6. The method according to claim 5, wherein simultaneously labelling the telomeres and centromeres further comprises, after the formaldehyde treatment,
a single step of treating the cytogenetic slide with pepsin for 3-5 minutes, by immersing a cytogenetic slide previously treated with formaldehyde in a pepsin solution at a concentration of 0.1-0.2 µg/mL.

7. The method according to claim 6, wherein simultaneously labelling the telomeres and centromeres further comprises, after the pepsin treatment step, the following steps of:
dehydrating the cytogenetic slide successively for 1 minute with a 50% aqueous ethanol solution, a 70% aqueous ethanol solution and pure ethanol;
denaturation the chromosomal DNA present on the above said cytogenetic slide obtained at the end of the previous step and denaturing the peptide nucleic acid probes for telomeres and centromeres;
hybridization for 10-30 minutes, at room temperature, between the denatured chromosomal DNA and the denatured peptide nucleic acid probes obtained in the previous step; and
successively washing said cytogenetic slide after hybridization.

8. The method according to claim 1, wherein a first peptide nucleic acid probe labels the telomeres and a second peptide nucleic acid probe simultaneously labels the centromeres, the first probe and the second probe emitting a distinctive fluorescence respectively.

9. The method according to claim 1 for chromosomal aberration detections, said method comprising:
labelling the telomeres and centromeres of metaphase cells with a ready-to-use solution of the nucleic acid probes;
automatically capturing fluorescent signals of the telomere and centromere labelling; and
analysing an image obtained in the previous step to obtain a data set: counting a number of centromeres in the metaphase, identifying each chromosome from its size and a ratio between short arm and the long arm, quantifying a signal of each telomere and centromere of each metaphase chromosome, for a detection of structural chromosome aberrations such as dicentric chromosomes, centric rings, acentric rings and different types of acentric chromosomes.

10. The method according to claim 1 for detecting micronuclei and anaphase bridges, said method comprising:
(i) labelling the telomeres and centromeres of interphase cells with a ready-to-use solution of the nucleic acid probes;
(ii) automatically capturing a fluorescent signals from the telomere and centromere labelling;
(iii) analysing an image obtained in step (ii) to obtain a data set: total number of micronuclei, number of micronuclei with only telomeric sequences, and number of micronuclei with both telomeric and centromeric sequences; and
(iv) analysing the image obtained in step (ii) to obtain the data set: identification of anaphase bridges by detecting the presence of a DNA filament connecting two daughter cells, length of the bridges, detection of a presence or an absence of centromeric or telomeric sequences in the bridges, counting total number of cells adhered.

11. The method according to claim 5, wherein the single step of treating a cytogenetic slide laps for 2 minutes with a 2-5% formaldehyde solution.

12. The method according to claim 5, wherein the single step of treating a cytogenetic slide laps for 2 minutes with a 4% formaldehyde solution.

13. The method according to claim 6, wherein the single step of treating the cytogenetic slide laps for 4 minutes.

14. The method according to claim 6, wherein the hybridization laps for 20 minutes.

15. The method according to claim 9, further comprising DAPI banding performed on the same metaphases, to complete the identification of chromosomes and detect single translocations.

16. The method according to claim 9, further comprising M-FISH labelling on the same metaphases, for multicolour karyotyping to detect complex rearrangements.

17. The method according to claim 9, wherein analysing the image allows classification of the chromosomes.

* * * * *